United States Patent
Gealow

[19]

[11] Patent Number: 6,063,115
[45] Date of Patent: May 16, 2000

[54] CARDIAC ASSISTANCE SYSTEM

[75] Inventor: Kendra Gealow, Meerssen, Netherlands

[73] Assignee: Medtronic, Inc., Minneapolis, Minn.

[21] Appl. No.: 08/834,012

[22] Filed: Apr. 11, 1997

[51] Int. Cl.[7] .................................................. A61M 1/10
[52] U.S. Cl. ........................................... 623/3.12; 600/16
[58] Field of Search ............................ 623/2, 3.12, 3.27; 600/16, 17

[56] References Cited

U.S. PATENT DOCUMENTS

| | | | |
|---|---|---|---|
| 4,902,291 | 2/1990 | Kolff | 600/16 |
| 4,979,936 | 12/1990 | Stephenson et al. | 600/16 |
| 4,994,078 | 2/1991 | Jarvik | 623/3 |
| 5,007,927 | 4/1991 | Badylak et al. | 623/3 |
| 5,205,810 | 4/1993 | Guiraudon et al. | 623/3 |
| 5,758,664 | 6/1998 | Campbell et al. | 600/16 |

FOREIGN PATENT DOCUMENTS

| | | |
|---|---|---|
| WO96/40307 | 12/1996 | WIPO . |
| WO96/40312 | 12/1996 | WIPO . |

OTHER PUBLICATIONS

"Skeletal Muscle Ventricles"—Seminars in Thoracic and Cardiovascular Surgery, vol. 3, No. 2 (Apr., 1991: pp. 154–159) –A. Pochettino et al..

*Primary Examiner*—Bruce Snow
*Attorney, Agent, or Firm*—Thomas F. Woods; Harold Patton; Michael J. Jaro

[57] ABSTRACT

A system to provide cardiac assistance to a patient's heart. The system includes a pulse generator adapted to be coupled to patient's heart and adapted to be coupled to a skeletal muscle ventricle (SMV). The system further includes a sewing ring adapted to be coupled to the SMV and adapted to be coupled to the patient's circulatory system, the sewing ring has a first annular ring and a second annular ring, the first and second annular rings having means for limiting the formation of tissue fibrosis in the vicinity of the first and second annular rings. In the preferred embodiment this comprises means for being more flexible at a distal end than a proximal end, which is accomplished by providing a series of holes in each of the rings. The holes preferably have a range of diameters, the holes located furthest away from the distal end of each ring have smaller diameters than compared to those holes located nearer to the distal end of the same ring.

19 Claims, 4 Drawing Sheets

CARDIAC ASSISTANCE SYSTEM

FIELD OF THE INVENTION

This invention relates to the field of cardiac assistance systems and particularly to a cardiac assistance system having an improved sewing ring to couple a skeletal muscle ventricle to the circulatory system of a patient.

BACKGROUND OF THE INVENTION

Cardiac assistance system provide additional cardiac output in patients who suffer from insufficient cardiac output. One type of cardiac assistance system is called a left ventricular assist device (LVAD). LVADs are auxiliary pouches intended to function as booster pumps to aid the hearts of individuals suffering from chronic congestive heart failure. This condition is frequently due to heart attacks that reduce the pumping capacity of the human heart. By boosting the capacity of such a weakened heart, individuals suffering from this condition may be allowed to again lead relatively normal, effective lives.

While various designs of LVADs have been proposed, the most promising appears to be an auxiliary pouch formed from the individual's latissimus dorsi muscle and controlled by a pacemaker. This approach avoids potential rejection problems related to the use of non-autologous materials and takes advantage of well developed pacemaker and prosthetic vascular graft technology. LVADs of this type are commonly called skeletal muscle ventricles (SMVs).

To create an SMV in a human involves exposing the left latissimus dorsi muscle and dissecting the muscle free from the subcutaneous tissues and chest wall, except for the neurovascular bundle and humeral insertion. A bipolar nerve cuff electrode is placed around the thoracodorsal nerve. The nerve lead is connected to an inactive neurostimulator, buried beneath the left rectus abdominis muscle, which innervates the exposed latissimus dorsi muscle.

Next, the left chest is opened at the fourth rib. Preferably, the fourth rib is removed to provide more space for the LVAD. Optionally, the anterior pericardium is removed between the phrenic nerves and used to cover a conically-shaped mandrel of biocompatible plastic. Mandrels used for beagles had a diameter of about 3 cm, length of about 6.5 cm and volume of about 25 ml; a mandrel suitable for forming a human SMV would need to be appropriately enlarged. After wrapping the pericardium around the mandrel it is sewn to a 5 mm thick collar of synthetic material such as woven DACRON felt placed at the base of the mandrel. The dorsal edge of the latissimus dorsi muscle is then folded longitudinally upon itself and secured by sutures, after which the medial aspect of the latissimus dorsi muscle is wrapped around the mandrel (and over the pericardium if it was used) about 2–2.5 times with the folded edge of the muscle sewn circumferentially to the Dacron felt collar. The SMV is then positioned DACRON and the wound is closed and allowed to heal for three weeks.

Following this healing period, a stimulator such as the Medtronic Model 4710 is activated to transform the fatigable Type II latissimus dorsi muscle fibers to fatigue-resistant Type I muscle fibers. Typically, 6 weeks are allowed for this stimulation period, after which the chest is again opened to connect the formed muscle pouch to the aorta. This is accomplished by first attaching sensing leads to the left ventricle. The descending thoracic aorta is exposed to allow two 12 mm ringed vascular grafts to be anastomosed to the aorta, one above the other, in end-to-side fashion.

After completion of these anastomoses, the aorta between the two graft anastomoses is at least partially ligated. The plastic mandrel is removed from within the muscle pouch and a sewing ring is used to couple the pouch to the aorta. The aorta is then at least partially ligated forcing blood flow through the newly formed SMV. Finally, the nerve lead and myocardial leads are connected to an R-wave synchronous pulse-train stimulator.

One problem such past cardiac assist systems have faced, however, is with the sewing ring. In particular, because the sewing ring is a foreign object to the body, the body's immune system often vigorously attacks it. A common result is that the object and the surrounding tissue develop a layer of fibrous tissue. Fibrous tissue around the sewing ring and within the skeletal muscle ventricle diminishes the ability of the SMV to pump blood. Another problem which may occur is the rupture of the SMV near the sewing ring. Such a rupture, in fact, is more likely to occur the more the sewing ring has been encapsulated by such fibrous tissue, as opposed to being well-incorporated by the skeletal muscle. Thus there exists a need for a sewing ring which will minimize the formation of fibrous tissue about the ring and in the surrounding SMV tissue.

SUMMARY OF THE INVENTION

This and other problems are solved by the present invention which is a system to provide cardiac assistance to a patient's heart. The system includes a pulse generator adapted to be coupled to patient's heart and adapted to be coupled to a skeletal muscle ventricle (SMV). The system further includes a sewing ring adapted to be coupled to the SMV and adapted to be coupled to the patient's circulatory system, the sewing ring has a has a first annular ring and a second annular ring, the first and second annular rings having means for limiting the formation of tissue fibrosis in the vicinity of the first and second annular rings. In the preferred embodiment this comprises means for being more flexible at a distal end than a proximal end, which is accomplished by providing a series of holes in each of the rings. The holes preferably have a range of diameters, the holes located furthest away from the distal end of each ring have smaller diameters than compared to those holes located nearer to the distal end of the same ring.

The FIGs. are not necessarily to scale.

DETAILED DESCRIPTION OF THE PREFERRED EMBODIMENTS

Figure 1:
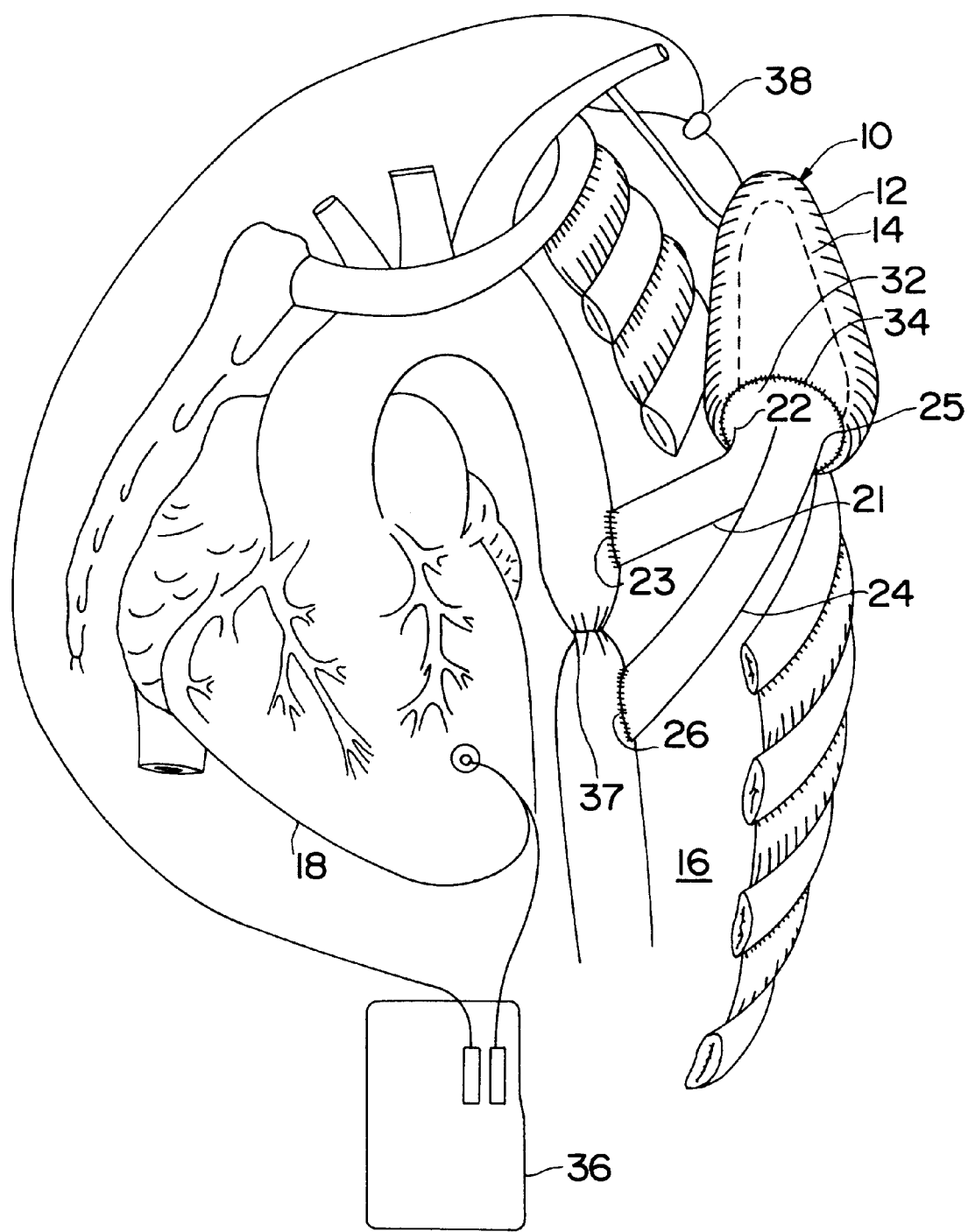
FIG. 1 describes a complete, functional LVAD.

FIG. 1 describes a typical cardiac assistance system in which a SMV 12, formed previously around a temporary mandrel to create a cavity 14, is connected to a patient's aorta 16 by ends 23 and 26 of vascular grafts 21 and 24. Opposing first ends 22 and 25 of vascular grafts 21 and 24 are sewn to a synthetic sheet of circular patch material 32 which is in turn sewn to SMV 12 at suture line 34. Ligation 37 is placed about the aorta 16 between adjacent second ends 23 and 26 of vascular grafts 21 and 24 so that the flow of blood from the heart 18 is routed through the SMV 12. Pulsing of the SMV 12 is controlled by burst pulse generator 36 connected to the heart 18 and the thoracodorsal nerve 38.

Two surgical procedures are used to create the cardiac assistance system 10. The first surgery involves wrapping the freed end of the strip of latissimus dorsi muscle around a plastic mandrel to form the SMV. The second surgery to remove the mandrel from the SMV 12 includes the subsequent steps of sewing the circular patch material 32 to the SMV 12 and anastomosing the vascular grafts 21 and 24 to aorta 16 and the circular patch 32. After completion of these steps the LVAD is activated before closing the patient's chest.

Figure 2A:
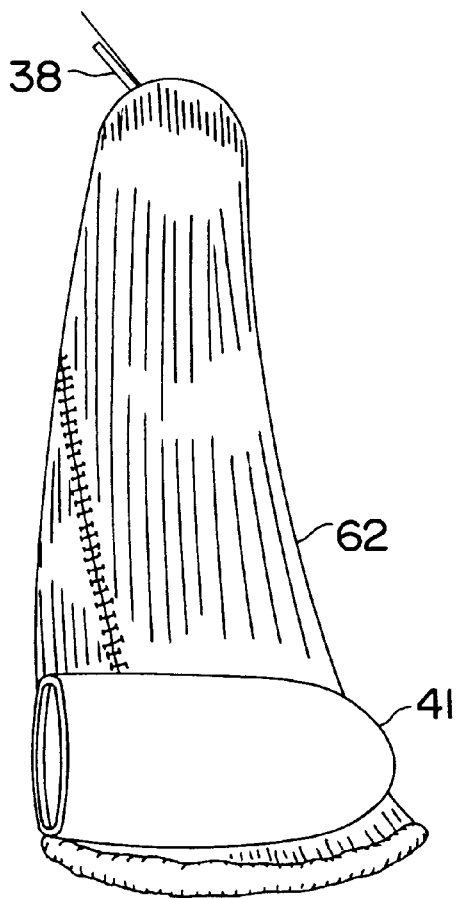
FIGS. 2A and 2B describe forming the SMV by wrapping latissimus dorsi muscle with or without optional pericardium around a mandrel.
Figure 2B:
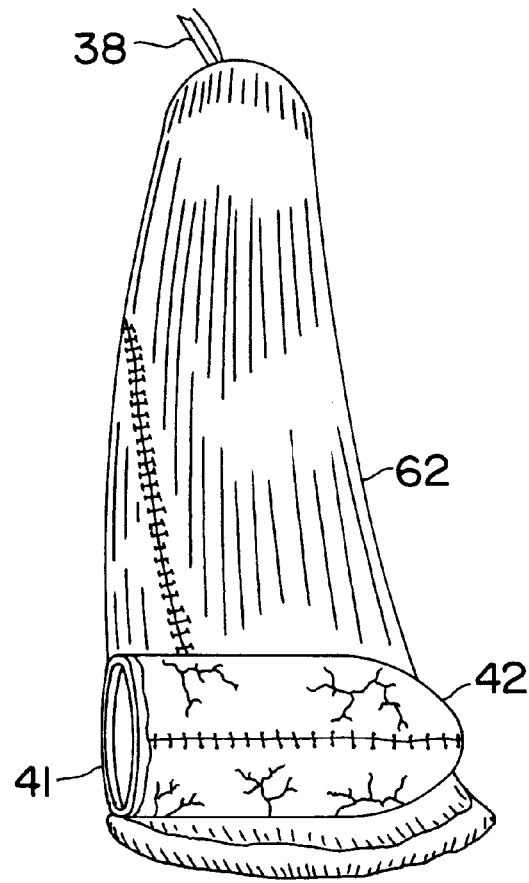

As seen in FIG. 2A, the latissimus dorsi muscle 62 is wrapped around the mandrel 41; typically 2–2.5 wraps of latissimus dorsi muscle are used. FIG. 2B describes an alternative whereby a sheet of anterior pericardium 42, previously removed from between the phrenic nerves, is wrapped around mandrel 41 prior to wrapping the latissimus dorsi muscle 62 around mandrel 41 to create the SMV 12.

Figure 3:
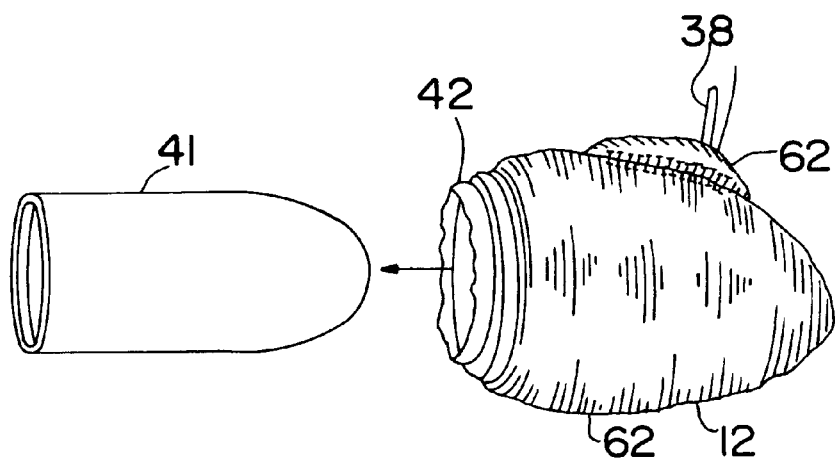
FIG. 3 describes removal of the mandrel from the SMV.

As shown by FIG. 3, after the SMV 12 has been completed by sewing the latissimus dorsi muscle 62 to itself, mandrel 41 is removed from the SMV 12.

Figure 4:
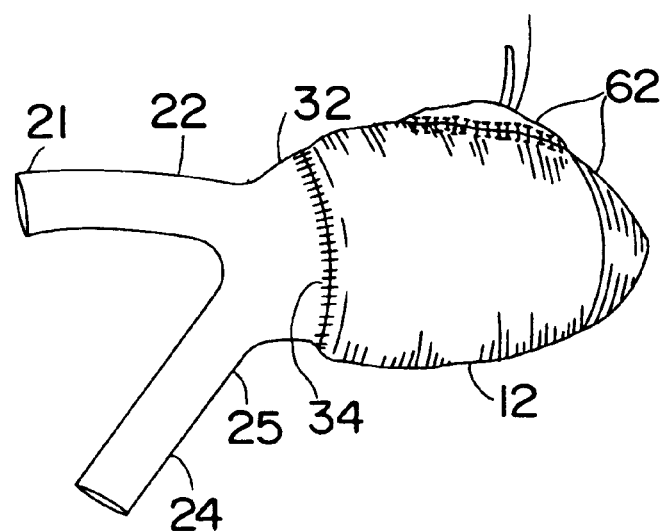
FIG. 4 describes the completed SMV after attachment to the circulatory system.

As shown in FIG. 4, once mandrel 41 is removed from the SMV 12, SMV is attached to vascular grafts 21 and 24 using a sewing ring. The edge of circular patch 32 is sewn at suture line 34 to the latissimus dorsi muscle 62 and to the pericardium 42 if pericardium is used.

Figure 5:
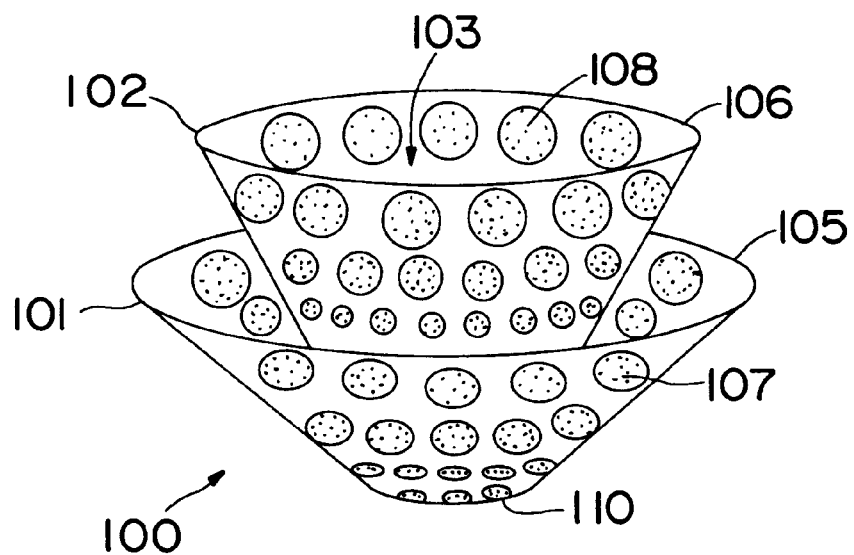
FIG. 5 is a perspective view of the sewing ring according to the present invention.

FIG. 5 is a perspective view of the sewing ring 100 according to the present invention. As seen, the sewing ring features an inner annular ring 102 and an outer annular ring 101. A lumen 103 is defined through the respective rings (best seen in FIG. 6.) Lumen is circular in the preferred embodiment although other shapes may also be used, e.g. elliptical. Outer annual ring 101 extends from root portion 110 to distal end 105. Inner annular ring 102 extends from root portion 110 to distal end 106. In the preferred embodiment the outer annular ring is not as long as the inner annular ring. Of course, the length of inner and outer ring must not be necessarily different such that inner and outer ring may have equal lengths. Moreover, it is also within the scope of the invention that inner ring is longer than outer ring. As seen, the outer annular ring features a series of holes 107. In the preferred embodiment holes 107 are present on ring from near root portion to near distal end 105. In the preferred embodiment these. holes have a range of diameters with the smallest diameter holes located closest to root portion and the largest diameter holes located farthest from root portion. In the preferred embodiment holes have a range between 1 to 5 mm, although other sizes may also be used, depending on the patient. Likewise, inner annular ring also has a series of holes, the diameter smallest nearest the root portion and greatest nearest distal end 108. In the preferred embodiment holes are circular and between 1 to 5 mm in diameter, although other sizes and shapes may also be used.

As mentioned above, these holes are essential to the operation of the present invention. Implanted objects are often encased by fibrotic tissue by the body. Fibrotic tissue tends to cause such objects to be stiff and inflexible. The fibrotic tissue response is in direct relationship to the material-tissue contact. Through the provision of the holes on the sewing ring less material is available to contact the tissues, thus less fibrotic tissue will develop. In addition, because the holes have their greatest diameter at the distal end of the respective annular rings, less material is near the distal end and the distal ends therefore will naturally be less stiff than root portion 110. Thus the absence of material towards the distal ends of the sewing rings provide both sewing rings flexibility at its distal ends and, because less foreign material is present, less fibrotic tissue response will occur. In addition, tissue growth through the holes will provide for better incorporation of the sewing ring by the skeletal muscle, thereby reducing the risk of rupture. In the preferred embodiment ring is constructed using DACRON felt. Of course other biocompatible materials may also be used, such as DACRON mesh or collagen or expanded PTFE (porous or non-porous), for example.

Figure 6:
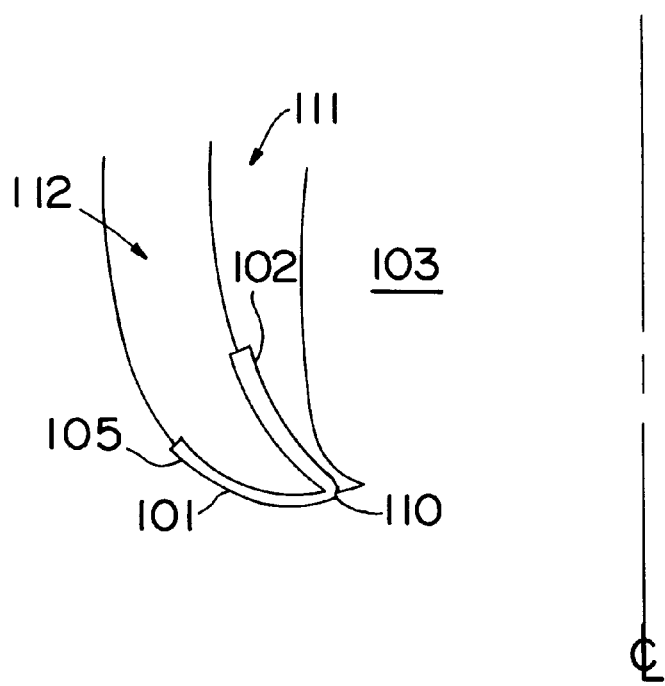
FIG. 6 is a cross-sectional view of one wall of sewing ring shown in FIG. 5.

FIG. 6 is a cross-sectional view of one wall of sewing ring 100. As seen, outer annular ring 101 extends away from root portion 110. Also extending from root portion 110 is inner annular ring 102. Inner annular ring extends at a smaller angle relative to the axis of the sewing ring as compared to outer annular ring. As seen, these rings are incorporated to provide the area into which the skeletal muscle used to form the SMV may be positioned and fixed. Likewise, the inner surface and inner annular ring may also be used to position and fix skeletal muscle. In the preferred embodiment inner skeletal muscle layer 111 of the SMV is fixed using sutures to the inner annular ring 102 while outer skeletal muscle layer 112 is fixed using sutures to the outer annular ring 101.

Sewing ring of the present invention may further feature the incorporation of pharmacological agents to permit healing and adhesion of the muscle to the ring. Such agents would include growth factors or anti inflammatory agents, such as various steroids, for example. Moreover, additional agents to inhibit thrombogenesis or calcification may likewise be incorporated into the fabric, such as a fibrin glue coating or attaching various bioactive molecules, such as heparin, for example.

Figure 7:
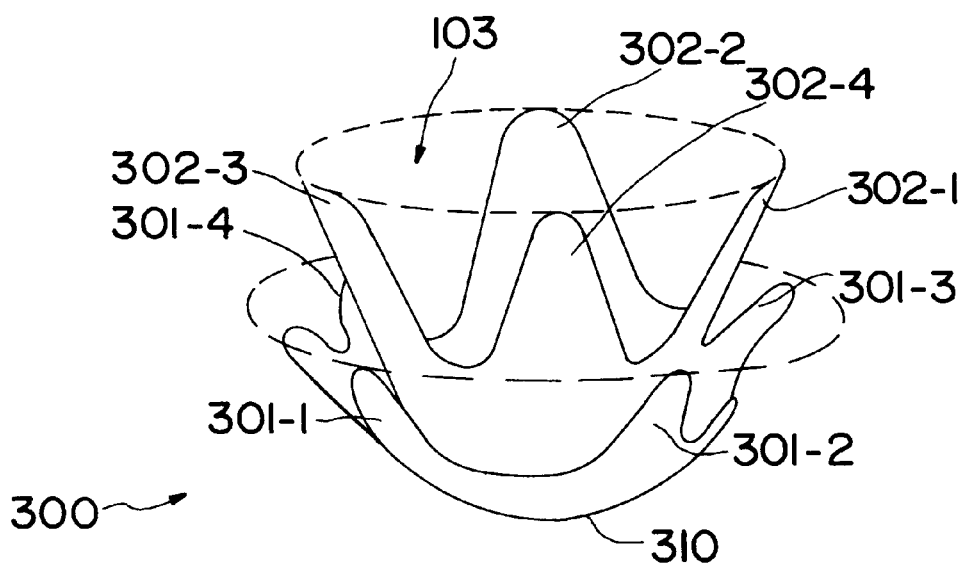
FIG. 7 is a perspective view of an alternative embodiment of a sewing ring.

FIG. 7 is a perspective view of an alternative embodiment of a sewing ring 300 according to the present invention. As seen, this embodiment provides for a decreased amount of material towards the ends of each flange through a ray like design. That is the ring an inner annular ring 302 and an outer annular ring 301. A lumen 303 is defined through the respective rings (best seen in FIG. 6.) Outer annual ring 301 extends from root portion 310 to distal end 305. Inner annular ring 302 extends from root portion 310 to distal end 336. Each ring moreover has a ray-like or crenellated design and is fashioned through a series of petals. Thus inner annular ring 302 is formed through petals 302-1, 302-2, 302-3 and 302-4. Outer annular ring 301 is formed through petals 301-1, 301-2, 301-3 and 301-4. Of course the particular number of petals used may be varied, as well as their spacing (i.e. uniform about lumen of grouped, for example.) Moreover, the specific shape of each petal may also be varied and they need not have the rounded shape as shown. Of course, the length of inner and outer ring must not be necessarily different such that inner and outer ring may have equal lengths. Moreover, it is also within the scope of the invention that inner ring is longer than outer ring. Through the provision of the petal construction less material is available to contact the tissues, thus less fibrotic tissue will develop. This absence of material towards the distal ends of the sewing rings provide both greater flexibility at its distal ends and, because less foreign material is present, less fibrotic tissue response will occur. In addition, tissue growth between the petals will provide for better incorporation of the sewing ring by the skeletal muscle, thereby reducing the risk of rupture. In the preferred embodiment ring is constructed using DACRON felt. Of course other biocompatible materials may also be used, such as DACRON mesh or collagen or expanded PTFE (porous or non-porous), for example.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A system for providing cardiac assistance to a patient's heart comprising a pulse generator adapted to be coupled to patient's heart and adapted to be coupled to a skeletal muscle ventricle; and a sewing ring adapted to be coupled to the skeletal muscle ventricle and adapted to be coupled to the patient's circulatory system, the sewing ring having a first annular ring and a second annular ring, the first and second annular rings having means for limiting the formation of tissue fibrosis in the vicinity of the first and second annular rings, the sewing ring having a root portion, the first and second annular rings connected to the root portion, wherein first annular ring has means for being more flexible at a distal end than a proximal end.

2. A system for providing cardiac assistance to a patient's heart according to claim 1 wherein first annular ring has a first length and second annular ring has a second length.

3. A system for providing cardiac assistance to a patient's heart according to claim 1 wherein the flexible means comprise a plurality of holes.

4. A system for providing cardiac assistance to a patient's heart according to claim 3 wherein the plurality of holes have a range of diameters, the holes located furthest away from the distal end have smaller diameters than compared to those holes located nearer to the distal end.

5. A system for providing cardiac assistance to a patient's heart according to claim 1 wherein second annular ring is more flexible at a distal end than a proximal end.

6. A system for providing cardiac assistance to a patient's heart according to claim 1 wherein second annular ring has means for being more flexible at a distal end than a proximal end.

7. A system for providing cardiac assistance to a patient's heart according to claim 6 wherein the flexible means comprise a plurality of holes.

8. A system for providing cardiac assistance to a patient's heart according to claim 7 wherein the plurality of holes have a range of diameters, the holes located furthest away from the distal end have smaller diameters than compared to those holes located nearer to the distal end.

9. A system for providing cardiac assistance to a patient's heart comprising a pulse generator adapted to be coupled to patient's heart and adapted to be coupled to a skeletal muscle ventricle; and a sewing ring adapted to be coupled to a the skeletal muscle ventricle and adapted to be coupled to the patient's circulatory system, the sewing ring having a first annular ring having means for limiting the formation of tissue fibrosis in the vicinity of the first annular ring, wherein first annular ring has means for being more flexible at a distal end than a proximal end.

10. A system for providing cardiac assistance to a patient's heart according to claim 9 further comprising the sewing ring having a root portion, the first annular ring extending away from the root portion a first angle relative to a center axis of the sewing ring, the sewing ring further comprising a second annular ring, the second annular ring extending away from the root portion a second angle relative to the center axis of the sewing ring.

11. A system for providing cardiac assistance to a patient's heart according to claim 10 wherein first annular ring has a first length and second annular ring has a second length.

12. A system for providing cardiac assistance to a patient's heart according to claim 9 wherein the flexible means comprise a plurality of holes.

13. A system for providing cardiac assistance to a patient's heart according to claim 12 wherein the plurality of holes have a range of diameters, the holes located furthest away from the distal end have smaller diameters than compared to those holes located nearer to the distal end.

14. A system for providing cardiac assistance to a patient's heart according to claim 10 wherein second annular ring is more flexible at a distal end than a proximal end.

15. A system for providing cardiac assistance to a patient's heart according to claim 10 wherein second annular ring has means for being more flexible at a distal end than a proximal end.

16. A system for providing cardiac assistance to a patient's heart according to claim 15 wherein the flexible means comprise a plurality of holes.

17. A system for providing cardiac assistance to a patient's heart according to claim 16 wherein the plurality of holes have a range of diameters, the holes located furthest away from the distal end have smaller diameters than compared to those holes located nearer to the distal end.

18. A system for providing cardiac assistance to a patient's heart according to claim 10 wherein the flexible means comprise a series of petals disposed about the lumen.

19. A system for providing cardiac assistance to a patient's heart according to claim 10 wherein the first annular ring is crenallated.

\* \* \* \* \*